United States Patent
Easson et al.

(10) Patent No.: US 8,551,529 B2
(45) Date of Patent: Oct. 8, 2013

(54) COMPOSITION FOR THE PRODUCTION OF TABLETS, AND METHOD FOR THE PRODUCTION OF SAID COMPOSITION

(75) Inventors: James Easson, Darmstadt (DE); Walter Hamm, Weiterstadt (DE); Guenter Moddelmog, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/382,957

(22) PCT Filed: Jul. 7, 2010

(86) PCT No.: PCT/EP2010/004135
§ 371 (c)(1),
(2), (4) Date: Jan. 9, 2012

(87) PCT Pub. No.: WO2011/003603
PCT Pub. Date: Jan. 13, 2011

(65) Prior Publication Data
US 2012/0100219 A1   Apr. 26, 2012

(30) Foreign Application Priority Data

Jul. 10, 2009 (EP) ................................... 09009065

(51) Int. Cl.
*A61K 31/405* (2006.01)
*A61K 33/42* (2006.01)
*A61K 9/20* (2006.01)

(52) U.S. Cl.
USPC .......................................... 424/489; 514/419

(58) Field of Classification Search
None
See application file for complete search history.

(56) References Cited

U.S. PATENT DOCUMENTS

| 2004/0162333 | A1* | 8/2004 | Mezaache et al. ............. 514/419 |
| 2005/0031682 | A1* | 2/2005 | Cucala Escoi et al. ....... 424/464 |
| 2009/0087485 | A1  | 4/2009 | Pilgaonkar et al. |

FOREIGN PATENT DOCUMENTS

WO   WO-2008 024044   2/2008

OTHER PUBLICATIONS

International Search Report for PCT/EP2010/004135 dated Jan. 9, 2012.

* cited by examiner

*Primary Examiner* — Janet Epps-Smith
*Assistant Examiner* — Yanzhi Zhang
(74) *Attorney, Agent, or Firm* — Millen, White, Zelano, Branigan, P.C.

(57) ABSTRACT

The present invention relates to a process for the preparation of a composition for the production of tablets and to a composition obtained thereby. This composition is a directly compressible composition which results both in improved tabletting properties and in improved tablet properties.

11 Claims, 5 Drawing Sheets

COMPOSITION FOR THE PRODUCTION OF TABLETS, AND METHOD FOR THE PRODUCTION OF SAID COMPOSITION

The present invention relates to a process for the preparation of a composition for the production of tables and to a composition obtained thereby. This composition is a directly compressible composition which results both in improved tabletting properties and in improved tablet properties.

Direct compression (DC) is a simple, rapid, inexpensive and flexible tablet production process which protects the active compound. For various reasons, however, not all components which can be employed for the formulation of tablets are suitable for use in this process.

Owing to poor flow properties and lack of compressibility, pulverulent calcium hydrogenphosphate dihydrate, for example, usually cannot be employed as tablet vehicle in direct tabletting without special additives or treatments.

However, direct compression is on the one hand usual in tablet production for cost reasons. On the other hand, however, it is also used for the formulation of pressed tablets from calcium hydrogenphosphate dihydrate in order to avoid incompatibilities of components in the formulations.

In general, however, only calcium hydrogenphosphate dihydrates which have been specifically physically modified are suitable for use in this process. Owing to the brittle material character, however, the compressibility of these materials is frequently inadequate in many formulations. In addition, the disintegration times of the pressed tablets produced from these DC calcium hydrogenphosphate dihydrates are in some cases unsatisfactory, due inter alia to the low solubility of calcium hydrogenphosphate dihydrate in aqueous media. DC calcium hydrogenphosphate dihydrates also have organoleptic disadvantages owing to the sandy, sharp-edged particle structure and the poor solubility, meaning that their use in orally disintegrating administration forms is restricted. Furthermore, the brittleness of these materials often results in high ejection forces in the tabletting moulds, together with increased wear of the compression moulds, but also in increased machine stress, with the associated down times and acquisition of replacements.

The object of the present invention is thus to provide a process by means of which problematic active compounds and assistants can also be converted into tablets by direct compression in a process. A further object of the present invention consists in preparing from the corresponding active compounds and assistants free-flowing, readily compressible compositions which can be pressed to give tablets in a simple manner.

The present object is achieved per se by preparing free-flowing, readily compressible compositions which allow direct compression, even with addition of less readily tablettable formulation components, by skillful combination and/or physical modification of the principal constituents of a tablet formulation. In particular, the properties of the various added components are utilised in such a way that these DC materials can be processed simply, are physiologically and chemically inert and can be converted, even with the lowest possible pressing forces, into tablets having very good tablet hardnesses at the same time as adequately fast disintegration times.

The present invention accordingly relates to a directly compressible composition for the production of tablets, which is characterised in that it consists of calcium hydrogenphosphate dihydrate and a flexible tabletting assistant.

This directly compressible composition for the production of tablets consists, in particular, of calcium hydrogenphosphate dihydrate and at least one polyol.

This composition particularly preferably consists of calcium hydrogenphosphate dihydrate and at least one polyol selected from the group mannitol, sorbitol, xylitol and erythritol. This composition particularly preferably comprises calcium hydrogenphosphate dihydrate and the polyols mannitol and sorbitol.

Good properties are found for directly compressible compositions if, for the production of tablets, calcium hydrogenphosphate dihydrate, mannitol and sorbitol are co-spray-granulated in advance in a weight ratio in the range from 50:40:10 to 85:10:5.

Particularly good properties have become apparent if calcium hydrogenphosphate dihydrate, mannitol and sorbitol are combined with one another in a weight ratio in the range from 60:30:10 to 70:20:10 for the preparation of this directly compressible composition for the production of tablets.

Directly compressible compositions, as described here, are distinguished by a flow angle in the range from 29 to 42°, in particular from 29 to 35°, particularly preferably in the range from 29 to 30°, making them particularly suitable for individual metering into the dies of the tabletting machines during tabletting or for sachet filling by machine.

Directly compressible compositions according to the invention have a bulk density in the range 0.55-0.75 g/ml with a tapped density in the range 0.73-0.90 g/ml. These properties of the pulverulent, directly compressible composition are combined with a particle-size distribution of 8 to 47% by weight in the range from 50 to 100 µm, 30 to 68% by weight in the range 100 to 200 µm, 6 to 44% by weight in the range from 200 to 315 µm and 0.6 to 12% by weight in the range 315-500 µm, where the proportion by weight of the particle-size fraction <50 µm is not more than 7% by weight and the proportion by weight of the particle-size fraction >500 µm is not more than 4% by weight. The composition advantageously has a high calcium content in the range from 11 to 20% by weight. If the composition according to the invention is compressed with a pressing force of 20 kN, tablets having hardnesses of >250 N are obtained, together with an ejection force of <210 N, a friability of <0.12%, a disintegration time of <735 seconds. In particular, pressed tablets having hardnesses of >300 N are obtained after compression with a pressing force of 20 kN, together with an ejection force of <110 N, a friability of <0.06% and a disintegration time of <620 seconds. If the composition according to the invention is compressed with a pressing force of 30 kN, pressed tablets having hardnesses of >430 N are obtained, together with an ejection force of <130 N, a friability of at most 0.08% and a disintegration time of <480 seconds. The present invention accordingly also relates to a composition or formulation which comprises the directly compressible composition characterised in this way and is in solid form or in the form of a compressate. A composition or formulation of this type may comprise one or more homogeneously distributed, water-insoluble and/or water-soluble additives. These additives are preferably selected from the group pharmaceutical active compounds, plant extracts, sweeteners, dyes, citric acid, vitamins and trace elements. Furthermore, such a composition or formulation according to the invention may comprise one or more pharmaceutical active compounds from the group of the analgesics, but, in particular, also one or more sweeteners selected from the group acesulfame K, Aspartame®, saccharin, cyclamate, sucralose and neohesperidin DC.

The present invention also relates to a process for the preparation of these directly compressible compositions for the production of tablets in which a solution or suspension comprising calcium hydrogenphosphate dihydrate, mannitol and sorbitol in a weight ratio in the range from 50:40:10 to 85:10:5, preferably in a weight ratio in the range from 60:30:10 to 70:20:10, in water, where 4 parts of solid are dissolved or suspended in 4 parts of water, is subjected to a co-spray-granulation process, either batchwise or continuously in a fluidised-bed granulator.

Experiments have shown that the combination of brittle calcium hydrogenphosphate dihydrate with a comparatively rather flexible material, such as, for example, a polyol, results in significantly improved tablet quality, which is on the one hand evident from considerably improved compressibility, but on the other hand tablets having a fast tablet disintegration time are simultaneously obtained. In particular, it has been found that a correspondingly improved product can be obtained from a combination consisting of about 50-85% by weight of pulverulent calcium hydrogenphosphate dihydrate, about 10-30% by weight of mannitol and about 5-15% by weight of sorbitol. In particular, a co-spray-granulation process gives a product for the direct-tabletting process which is optimum with respect to flow behaviour, compressibility, disintegration properties and other pharmaceutical formulation characteristics. The material according to the invention exhibits significantly better processing properties than would be possible, for example, by simple physical mixtures, even using directly tablettable individual components. It has furthermore been found that the pharmaceutical formulation properties of these co-sprayed products are only improved by the addition of a certain amount of sorbitol.

In addition, the ratio of the three constituents mentioned above must be kept within an optimised range in order to obtain the improved pressing force/hardness or hardness/disintegration time profiles. In particular, it has been found that the improved properties are obtained if the weight ratio is in a range between about 60:30:10 and 70:20:10, based on the ratio of calcium hydrogenphosphate dihydrate to mannitol to sorbitol. In this range, the corresponding compositions give particularly improved pressing force/hardness or hardness/disintegration time profiles. This composition apparently has a balanced ratio between the flexibility of the polyols and the brittleness of the calcium hydrogenphosphate dihydrate, which produces the very good pressing properties.

With the material obtained, the formulation pharmacist obtains a product which is optimised with respect to the direct-tabletting properties and with the aid of which active compounds which are poorly tablettable per se also become able to undergo this simple tabletting process. In addition, its high calcium and phosphate content means that the product is of interest for the formulation of calcium- and phosphorus-enriched pressed tablets, for example in chewable tablets for food supplementation. This use is also particularly appropriate since the material gives rise to very good sensory properties due to the extremely fine distribution of the finely divided calcium hydrogenphosphate dihydrate, which naturally has an unpleasant sandy taste and is virtually insoluble, in a matrix of the sweet- and cool-tasting polyols.

The present invention thus provides a directly compressible tabletting composition or a tabletting assistant based on calcium hydrogenphosphate dihydrate having improved properties which is obtained by co-spray-granulation of calcium hydrogenphosphate dihydrate, mannitol and sorbitol.

Corresponding assistants composed in accordance with the invention for the production of tablets, consisting of calcium hydrogenphosphate dihydrate/mannitol/sorbitol, which are obtained by co-spray-granulation, can be employed for the preparation of directly compressible tabletting compositions.

As can be concluded from the sensory properties of calcium hydrogenphosphate dihydrate, a very homogeneous distribution of the calcium hydrogenphosphate dihydrate, which is virtually insoluble in water at a neutral pH, in a matrix comprising the two water-soluble polyols mannitol and sorbitol is obtained. This homogeneous distribution can be achieved by a co-spray-granulation process of all components from aqueous solution or suspension in a fluidised bed.

Besides the pleasant sensory properties (mouth feel), the direct-compression properties may advantageously also be improved thereby.

In this connection, the co-spray-granulated compositions according to the invention, consisting of calcium hydrogenphosphate dihydrate, mannitol and sorbitol, exhibit a number of unexpected advantages:

1. Improved properties during compression to give tablets:

Whereas calcium hydrogenphosphate dihydrate and mannitol can usually be pressed to give tablets with some difficulty, the three-component combination calcium hydrogenphosphate dihydrate/mannitol/sorbitol has very good properties during direct compression, in particular if the components in certain mixing ratios are subjected to co-spray-granulation with one another in advance. The products obtained in this way can subsequently be converted into tablets having improved properties.

Particularly good pressing force/hardness ratios are found if the three components calcium hydrogenphosphate dihydrate, mannitol and sorbitol are co-spray-granulated with one another in a ratio in the range between 50:40:10 and 85:15:5, in particular in the range between 60:30:10 and 70:20:10. These mixing ratios apparently represent an optimum ratio of the brittle properties of the calcium hydrogenphosphate dihydrate and the plastic properties of a mannitol/sorbitol combination for compression during pressing. In experiments, particularly good properties were shown, in particular, by corresponding products in which calcium hydrogenphosphate dihydrate, mannitol and sorbitol were co-sprayed with one another in a mixing ratio of 60:30:10 or 70:20:10.

Compositions in which a higher proportion of calcium hydrogenphosphate dihydrate is employed during the co-spraying or in which the proportion of the polyols mannitol or sorbitol is increased for the co-spraying have worse compressibilities. However, even if only one of the two polyols is co-sprayed together with calcium hydrogenphosphate dihydrate in the compositions, this results in a decrease in the compressibility.

Compared with commercially available, directly compressible (DC) calcium hydrogenphosphate dihydrate, the properties of the three-component combinations, in particular of the two preferred three-component combinations in the mixing ratio 60:30:10 or 70:20:10, during direct compression are considerably improved. However, considerably improved properties are also apparent compared with a physical mixture consisting of commercially available DC calcium hydrogenphosphate dihydrate and the DC mannitol grades (Parteck M 200) and DC sorbitol (Parteck SI 150), which are very readily directly compressible per se, in the ratio 70:20:10.

2. Short (fast) disintegration times of the pressed tablets, even in high hardness ranges Co-spraying as a three-component combination comprising at least 50% by weight and at most 85% by weight of calcium hydrogenphosphate dihydrate at high tablet hardnesses without the addition of disintegration-promoting components (disintegrants) at the same time gives shorter disintegration times compared with compositions having the same tablet hardnesses which have been obtained by pressing mechanical mixtures at a higher pressing pressure. However, if the calcium hydrogenphosphate content is additionally increased in the co-spray-granulated composition, this further addition of dihydrate results in retardation of disintegration.

The two preferred compositions having a calcium hydrogenphosphate dihydrate:mannitol:sorbitol ratio of 60:30:10 or 70:20:10 exhibit short disintegration times over a significantly broader tablet-hardness range, to be precise comparatively significantly shorter disintegration times than of commercially available DC calcium hydrogenphosphate dihydrates pressed to give tablets or of corresponding pressed, physical mixtures with DC mannitol grades (Parteck M 200) and DC sorbitol (Parteck SI 150).

3. Mechanical stability of the resultant tablets

The mechanical stability of pharmaceutical formulations in the form of granules or tablets is assessed, inter alia, with reference to their friability. Friability is a measure in per cent by weight of the mechanical abrasion of the tablets under mechanical load. Tablets are subjected to physical loads from production to final consumption. They must therefore be developed in such a way that they survive the impacts arising with as little damage as possible.

In order to establish how the tablets to be tested survive these loads and in order to be able to draw conclusions on further processing (for example coating, sugar coating, packaging), friability or abrasion tests are therefore carried out. In these tests, the tablets are tested in accordance with the principle of a recurring movement in Roche friabilator or abrasion drums. The test conditions, such as number of samples, number of rotations and test speed, are defined in the pharmacopoeias. Abrasion is defined as the mass that the tablets lose due to the mechanical load.

In order to determine the friability, various instruments in different designs are commercially available. The ERWEKA TDR 100 tester is a semi-automatic combination system comprising an ERWEKA abrasion/friability tester and a Sartorius analytical balance. The system is controlled by the ERWEKA abrasion/friability tester (Erweka Apparatebau, Heusenstamm).

Other instruments are:

Model TAP No. 43651 friability tester, Erweka Apparatebau, Heusenstamm

Abrasion tester from Arzneimittelwerk Dresden, Dresden, Friabilator model PTF 1, Pharmatest, Roche friabilator, J. Engelsmann AG, Ludwigshafen/Rhein The friability of the tablets to be tested is tested in these instruments by methods as described in Ph. Eur. Supplement 2001 or Ph. Eur. 6th Edition, main part 2008, under "2.9.7 Friability of uncoated tablets".

For the assessment, a fixed number of dust-free tablets can be agitated in a drum with a chicane for a certain time and at a fixed speed. The mass loss of the dust-freed tablets is subsequently determined in per cent.

In the experiments of the present invention, the friability of the tablets produced by pressing was determined by investigating the abrasion of tablets in a Roche friabilator as described in Ph. Eur. 6th Edition, main part 2008, under 2.9.7. In each case, 100 rotations were carried out with the instrument, with the rotational speed being $25+/-1$ $min^{-1}$.

The measurements have shown that the friabilities of co-sprayed compositions having a calcium hydrogenphosphate dihydrate:mannitol:sorbitol ratio of 70:20:10, which have been converted into tablets at various pressing forces, are significantly lower than in the case of tablets in which DC calcium hydrogenphosphate dihydrate has been employed alone. In addition, no "capping" has been observed in these tablets according to the invention. Comparably improved results have been observed for co-spray-granulated compositions having a weight ratio of calcium hydrogenphosphate dihydrate:mannitol:sorbitol in the range between 50:40:10 and 85:10:5, in particular in the range between 60:30:10 and 70:20:10. Particularly good results have been found for compositions in which the ratio is in the range between 60:30:10 and 70:20:10. Owing to these improved properties, the present compositions enable very safe handling of the pressed tablets during further processing, for example in packaging machines or coating equipment, and can be safely handled by the patient on removal from blister packs.

4. Low ejection forces, i.e. protection of the punch dies and tabletting machines The compositions according to the invention have not only reduced friability, but the improved properties are also evident during tabletting. In particular, the requisite ejection forces are minimised in the tabletting of calcium hydrogenphosphate dihydrate/mannitol/sorbitol compositions according to the invention at all tested pressing forces. Minimised ejection forces are found, in particular, for calcium hydrogenphosphate dihydrate/mannitol/sorbitol compositions in the ratio 70:20:10. This means that optimum protection of the compression moulds and machines during this operation is achieved in the tabletting of a three-component combination composition of this type.

On use of compositions according to the invention during tabletting, these stuck neither to the punch nor to the dies of the tabletting machine nor between the punch and the dies. The compositions according to the invention also have no tendency to accumulate on the punches and dies and thus cause friction between the punch and the die. They can therefore be ejected from the tabletting dies with reduced pressure.

The compositions according to the invention can be processed industrially in a continuous and stable manner for a long time on corresponding tabletting machines without so-called rough running of the machines occurring.

Simply the preparation of the precursors for the production of tablets by co-spray-granulation of calcium hydrogenphosphate dihydrate, mannitol and sorbitol in the weight ratios according to the invention gives compositions having a high calcium hydrogenphosphate content, which can also be used for calcium and phosphorus enrichment in foods, as food supplements or in pharmaceutical preparations, in particular in the form of powder sachets, pressed tablets or in capsules. Furthermore, the flow angle of the material prepared is optimal for further processing, in the range from 29 to 42°, in particular from 29 to 35°, particularly preferably in the range from 29 to 30°. The material is thus, for example, eminently suitable for individual metering into the dies of the tabletting machines during tabletting or for sachet filling by machine.

In order to carry out the co-spray-granulation, aqueous solutions or suspensions of the various components are prepared in advance. 50% [50% (w/w)] solutions or suspensions are preferably used, where the per cent data relate to the respective percentages by weight. The dry substances are dissolved or suspended in demineralised water. In order to carry out the co-spray-granulation, the amount ratios of the calcium hydrogenphosphate dihydrate to the polyols mannitol and sorbitol are adjusted in solution in such a way that the desired ratios by weight arise in the ratio to one another according to the invention in the co-sprayed substance. For the preparation of the spray solution, the amount of demineralised water calculated in advance is initially introduced in a batch vessel. The polyols sorbitol and mannitol are stirred into the water at 20-25° C. until completely dissolved. The calcium hydrogenphosphate dihydrate is introduced into this clear solution, likewise with stirring, and the white suspension is stirred until any agglomerates formed have disintegrated. This solution/suspension is sprayed with constant stirring in the co-spray-granulation.

In order to obtain a calcium hydrogenphosphate dihydrate with the most homogeneous distribution possible in the polyol matrix, starting granules may firstly be produced in a batch process (pre-spraying), of which in each case a small amount can then be employed for initial introduction in the fluidised bed for one or more co-spray-granulation processes (main sprayings). In this way, the proportion of inhomogeneously distributed calcium hydrogenphosphate in the polyol matrix can continue to be reduced to a negligible proportion.

It is of course significantly simpler if the starting granules employed comprise co-sprayed material of the desired composition which has been removed from prior sprayings and can be initially introduced in the fluidised bed. The spraying is then carried out as described for the main spraying in the following examples.

The continuous preparation is carried out in a similar manner as described in the specifications EP 1 453 781 A1, EP 1 319 644 A1 and WO 00/76650 A1, for example for the preparation of alpha- or beta-mannitol. In particular, the continuous preparation of the compositions according to the invention is carried out in a fluidised-bed granulator with powder recycling and continuous removal of product, where the average particle size of the resultant product is controlled by the air stream in the fluidised bed.

This co-spray-granulation produces a very homogeneous distribution of the calcium hydrogenphosphate dihydrate, which is virtually insoluble in water at a neutral pH, in a matrix comprising the two water-soluble polyols mannitol and sorbitol. This homogeneous distribution is produced by a co-spray-granulation process of all components from aqueous solution or suspension in a fluidised bed. Besides a product having pleasant sensory properties (mouth feel), a product having very good direct-compression properties is also obtained in this way.

The principle of the co-spray-granulation process and the design of the equipment can be obtained from the patent specifications EP 1 453 781 (beta-mannitol), EP 1 319 644 (alpha-mannitol) and WO 00/76650.

The desired particle sizes can be produced by variation of the process parameters spray pressure, spray amount, recycled amount of powder, hot-air stream and hot-air temperature. If necessary, a particle-size restriction can also be carried out by sieve classification at the discharge. Coarse particles can be recycled into the spray system after comminution by a grinding fan.

In principle, the compositions according to the invention are prepared in a similar manner as described in the specifications EP 1 453 781 A1, EP 1 319 644 A1 for the preparation of alpha- and beta-mannitol or in WO 00/76650 A1. More precisely, the co-spray-granulation is carried out in a fluidised-bed granulator with powder recycling, in which the spraying of the solutions or suspensions is carried out by means of two-component nozzles, via which powder recycled simultaneously is transported into the spray zone.

For this purpose, the spray pressure of the two-component nozzles should be set in the range 2-4 bar, preferably in the range 2.5-3.5 bar. The amount of hot gas fed to the two-component nozzle should be regulated in such a way that up to about 1.5-3 $m^3/(h\ kg$ of suspension) is conveyed at a temperature of about 80-110° C.

The powder recycling should be set in such a way that solids recycling takes place in the range 0.2-2.0 kg of solid/(h kg of suspension), preferably in the range 0.5-1.5 kg of solid/(h kg of solution). The process is particularly favourable if the solids recycling is in the range 0.5-1.0 kg/(h kg of solution).

In order to carry out the process, pre-warmed air must be fed into the equipment. Good results are achieved if the air fed to the equipment is pre-warmed to a temperature in the range 45-120° C. It is favourable for the process according to the invention for the feed air to have a temperature in the range 65-110° C. It is particularly advantageous for the formation of co-spray-granulated calcium hydrogenphosphate/mannitol/sorbitol having good tabletting properties if the temperature of the air fed in is in the range 70-100° C. The amount of feed air supplied should be regulated in accordance with the invention in such a way that 1000-2000 $m^3/m^2$ per hour, in particular 1200-1700 $m^3/m^2$ per hour, are fed into the equipment.

In combination with the other parameters set, favourable process conditions exist if the air stream in the equipment is guided in such a way that the exhaust-air temperature becomes established in the range 30-50° C. and the temperature of the product formed becomes established at a temperature in the same range up to 50° C.

It has furthermore proven favourable to regulate the process conditions in such a way that the amount of powder located in the fluidised bed becomes established at an amount of bed of 50-150 $kg/m^2$ of bed. It is particularly favourable for the amount of bed to be in the range 80-120 $kg/m^2$ of bed.

Targeted powder recycling both by powder removal from the fluidised bed and also by recycling of a very fine powder fraction formed during formulation, i.e. homogenisation of the particle size by sieving during packaging of the product produced, enables the process to be controlled with respect to the desired particle-size distribution.

It is also possible to comminute powders having relatively large particle cross sections in the grinding fan of the spray-granulation unit before the recycling so long as a fluidised-bed granulator is used, as described in EP 1 453 781 A1 or EP 1 319 644 A1.

The special preparation procedure in a co-spray-granulation process gives directly compressible compositions having a bulk density in the range 0.55-0.75 g/ml and a tapped density in the range 0.73-0.90 g/ml. These properties are combined with a particle-size distribution of 8 to 47% by weight in the range from 50 to 100 μm, 30 to 68% by weight in the range 100 to 200 μm, 6 to 44% by weight in the range from 200 to 315 μm and 0.6 to 12% by weight in the range 315-500 μm, where the proportion by weight of the particle fraction <50 μm is not more than 7% by weight and the proportion by weight of the particle fraction >500 μm is not more than 4% by weight. Depending on the proportion by weight of co-sprayed polyol during the co-spray-granulation, the composition has a calcium content in the range from 11 to 20% by weight.

Investigations of the tabletting properties of the directly compressible compositions according to the invention have shown that the composition according to the invention can be compressed with a pressing force of 20 kN to give tablets having hardnesses of >250 N, together with an ejection force of <210 N, a friability of <0.12%, a disintegration time of <735 seconds. In particular, pressed tablets having hardnesses of >300 N are obtained after compression with a pressing force of 20 kN, together with an ejection force of <110 N, a friability of <0.06% and a disintegration time of <620 seconds. If, by contrast, the composition according to the invention is compressed with a pressing force of 30 kN, the pressed tablets have hardnesses of >430 N, together with an ejection force of <130 N, a friability of at most 0.08% and a disintegration time of <480 seconds.

In accordance with the invention, the directly compressible composition in accordance with the present invention can be introduced into a composition or formulation which is in solid form or in the form of a compressate. As pharmaceutically usable composition or formulation, this may in turn comprise one or more homogeneously distributed, water-insoluble and/or water-soluble additives. The homogeneous distribution can be produced either by prior intensive mixing with the directly compressible composition before the tabletting or packaging is carried out. However, the homogeneous distribution can also be achieved by joint co-spray-granulation under suitable conditions. The water-soluble or water-insoluble additives are selected, in particular, from the group pharmaceutical active compounds, plant extracts, sweeteners, dyes, citric acid, vitamins and trace elements. These additives are selected so that they are stable and capable of storage in the combination of the individual components of the composition. In particular, such a composition or formulation according to the invention may comprise one or more pharmaceutical active compounds from the group of the analgesics, but furthermore also one or more sweeteners, selected from the group acesulfame K, Aspartame®, saccharin, cyclamate, sucralose and neohesperidin DC, in order to improve the taste.

For better understanding and in order to illustrate the invention, examples are given below which are within the scope of protection of the present invention. These examples also serve to illustrate possible variants. Owing to the general validity of the inventive principle described, however, these examples are not suitable for reducing the scope of protection of the present application to these alone.

Should anything be unclear, the references and patent specifications cited in the description, which should hereby regarded as part of the disclosure content of the present invention, should also be used for better understanding.

The temperatures given in the following examples and description and in the claims are always in ° C. Unless stated otherwise, content data are quoted as % by weight or weight ratios.

It furthermore goes without saying to the person skilled in the art that, both in the example given and also in the remainder of the description, the component amounts present in the compositions always only add up to 100% by weight or mol-%, based on the composition as a whole, and cannot exceed this, even if higher values could arise from the per cent ranges indicated. Unless indicated otherwise, % data are taken to be % by weight, with the exception of ratios, which are shown in volume data.

EXAMPLES

In order to carry out the co-spray-granulation according to the invention, the following instruments and processes are employed for characterisation of the substance properties:

1. Bulk density: in accordance with DIN EN ISO 60: 1999 (German version)
   data in the tables as "g/ml"
2. Tapped density: in accordance with DIN EN ISO 787-11: 1995 (German version)
   data in the tables as "g/ml"
3. Angle of repose: in accordance with DIN ISO 4324: 1983 (German version)
   data in the tables as "degrees"
4. Hausner factor: calculation in accordance with Ph. Eur. 6th Edition, main part 2008, section 2.9.36 "Compressibility index and Hausner factor"
5. Compressibility index: calculation in accordance with Ph. Eur. 6th Edition, main part 2008, 2.9.36, "Compressibility index and Hausner factor"
   data in the tables as "%"
6. Tabletting testing: 492.5 g of the material whose tabletting properties are to be tested are mixed with 7.5 g of Parteck LUB MST (vegetable magnesium stearate) EMPROVE exp Ph. Eur., BP, JP, NF, FCC, Art. No. 1.00663 (Merck KGaA, Germany); the magnesium stearate is passed through a 250 μm sieve in advance and mixed for 5 minutes in a sealed stainless-steel container (capacity: about 2 l, height: about 19.5 cm, diameter: about 12 cm; external dimensions) in a laboratory tumble mixer (Turbula, Willy A. Bachofen, Switzerland). Pressing to give 500 mg tablets (11 mm punch, round, flat, with bevel) is carried out in an instrumented Korsch EK 0-DMS cam tabletting machine (Korsch, Germany) with Catman 5.0 evaluation system, Hottinger Baldwin Messtechnik—HBM (Germany).
   Depending on the pressing force (nominal settings: 5+/−1, 10+/−1, 20+/−2 and 30+/−2 kN; the effectively measured actual values are shown in the examples), at least 100 tablets are produced for evaluation of the pressing data and the pharmaceutical formulation characteristics.
7. Determination of the tablet hardness, diameter and height: Erweka TBH 30 MD; Erweka (Germany); average data from 20 tablet measurements per pressing force
8. Tablet abrasion: friability tester, Erweka (Germany); instrument parameters and performance of the measurements in accordance with Ph. Eur. 6th Edition, main part 2008, 2.9.7. "Friability of uncoated tablets"
9. Tablet weight: average value from the weighing of 20 tablets; balance: Mettler AT 201, Mettler (Germany)
10. Tablet disintegration: disi4 automatic disintegration tester from Biomation (Germany); medium: desalinated water at 37° C.; instrument parameters and performance in accordance with Ph. Eur. 6th Edition, "Disintegration time of tablets and capsules" (with disc)
11. Determination of the particle sizes as dry sieving via a Retsch AS 200 control 'g' sieve tower, Retsch (Germany); amount of substance: 40 g+/−2 g; sieving time: 30 minutes; amplitude: 1 mm; interval: 5 seconds; diameter of the sieve inserts used: 200 mm; sieve sizes: 1000, 710, 500, 315, 200, 100, 50 and 32 μm; amount distribution per sieve fraction indicated in the tables as "% by weight of the sample weight"
12. Calcium content determination: complexometric titration using Na EDTA solution and potentiometric indication or colour indication. The principle of the procedure is described in the technical literature, such as, for example, in G. Jander, K. F. Jahr, H. Knoll "Maβanalyse—Theorie und Praxis der klassischen und der elektrochemischen Titrier-verfahren" [Volumetric Analysis—Theory and Practice of Classical and Electrochemical Titration Methods], publisher Walter de Gruyter, 1973 ISBN 3 11 005934 7, or in the application documents from the titration and indicator electrode manufacturers, for example from Mettler-Toledo GmbH, Germany, or Metrohm, Switzerland.

Before the titration, the samples (sample weight about 0.2 g, weighed accurately) are slurried with a little demineralised water and dissolved using 5 ml of 25% hydrochloric acid. 20.00 ml of 0.1 mol/l Titriplex(III) solution (Art. No. 1.08431; MERCK KGaA, Germany) are metered in, the mixture is made up to 70 ml with demineralised water, a buffer tablet (Art. No. 1.08430, MERCK KGaA, Germany) is added, and, after the buffer tablet has dissolved, the pH is adjusted to 10-11 with stirring using about 10 ml of ammonium buffer solution pH 10-11 (Art. No. 1.09478, MERCK KGaA, Germany). The mixture is subsequently back-titrated potentiometrically with a zinc sulfate solution (0.1 mol/l). The calcium content can be calculated stoichiometrically from the consumed amount of 0.1 mol/l Titriplex (III) solution.

Raw Materials for the Preparation of the Compositions According to the Invention Calcium hydrogenphosphate dihydrate, very finely powdered, suitable for use as excipient EMPROVE® exp Ph. Eur., BP, USP, FCC, E 341 (Art. No. 1.02146, Merck KGaA, Germany)

Particle size: 99%<63 µm, measured by laser diffraction with wet dispersal

Instrument/method: Malvern Mastersizer 2000, Hydro 2000 S wet module, direct addition,
  evaluation model: universal,
  medium: demineralised water,
  refractive index: medium 1.33 (MIE parameters), Fraunhofer,
  stirring speed: 2000 rpm,
  ultrasound: 100%,
  obscuration: 10-20%,
  measurement duration: 7500 ms,
  performance in accordance with technical manual and manufacturer's specifications D(-)-mannitol suitable for use as excipient
EMPROVE® exp Ph. Eur., BP, USP, JP, FCC, E 321 (Art. No. 1.05980, Merck KGaA, Germany)

Parteck® SI 400 (sorbitol) suitable for use as excipient
EMPROVE® exp Ph. Eur., BP, NF, E 420 (Art. No. 1.03140, Merck KGaA, Germany)

Demineralised Water

Comparative Substances:

Parteck M200 (mannitol) suitable for use as excipient
EMPROVE® exp Ph. Eur., BP, JP, USP, E 421 (Art. No. 1.00419, Merck KGaA, Germany)

Parteck SI 150 (sorbitol) suitable for use as excipient
EMPROVE® exp Ph. Eur., BP, JP, NF, E 420 (Art. No. 1.03583, Merck KGaA, Germany)

Emcompress® Premium dibasic calcium phosphate dihydrate, USP, calcium hydrogenphosphate dihydrate, Ph. Eur. dibasic calcium phosphate, JP (JRS PHARMA GmbH & Co. KG, Germany), Batch No.: A71345A DI-CAFOS dicalcium phosphate 2-hydrate coarse powder, USP, FCC, Ph. Eur., JP, E 341 (Product No.: C 92-14, Chemische Fabrik Budenheim KG, Germany)

Material No. 00000809, Batch No.: B09094A

DI-TAB dicalcium phosphate dihydrate, unmilled USP, FCC, EP, E 341 (Innophos Inc., USA; purchased via Univar GmbH, Essen, Germany) batch 7016

General Performance of Co-Spray-Granulation

A solution or suspension of 4 parts of water and 4 parts of solid, where the solid consists of 6-7 parts of pulverulent calcium hydrogenphosphate dihydrate, 2-3 parts of mannitol and 1 part of sorbitol, or where the solid has the ratio of the pulverulent starting materials calcium hydrogenphosphate dihydrate, mannitol and sorbitol in the desired ratio of the composition to be prepared, is subjected to a granulation process (batchwise or continuous) in a fluidised-bed granulator. In order to prevent adhesive effects in the granulator, in particular also on use of a continuous process, partial solids recycling can be employed. A product having a defined particle-size distribution or bulk and tapped density can be obtained by an optional subsequent sieving process.

Preparation of the Spray Solutions or Spray Suspensions:

All spray solutions and suspensions were prepared as 50% solutions or suspensions, based on the weight of the dry substance and the weight of the demineralised water. The ratios of the calcium hydrogenphosphate dihydrate to the polyols arise from the desired compositions of the desired end products, as indicated in Table 1.

The polyols are stirred into the water initially introduced in a batch vessel at 20-25° C. until completely dissolved. The calcium hydrogenphosphate dihydrate is introduced into this clear solution, likewise with stirring, and the white suspension is stirred until any agglomerates formed have disintegrated. This solution/suspension is sprayed with constant stirring.

Preparation of the Starting Material for the Co-Spray-Granulation:

In order to start up the equipment, it is necessary to pass a primary amount of bed through the co-spray-granulation process. This starting bed can be produced in two ways:

1. The equipment is filled at the beginning of the spraying process with material retained from material previously co-sprayed in accordance with the invention or 2. The equipment is filled with a physical mixture of the desired components in the qualitative and quantitative composition to be prepared, i.e. with pulverulent calcium hydrogenphosphate dihydrate, mannitol and sorbitol. The co-spray-granulation process is carried out as described, but without removing material at the outlet. Instead, all the material is recycled into the process via a grinding fan until a stable process and a product composition according to the invention have been achieved. The establishment of the particle-size distribution is then begun with product removal, as described for a continuous process.

In order to illustrate the corresponding procedure, the example which results in the preparation of the co-sprayed composition called product E below is described. In order to obtain a starting material which can be employed for the co-spray-granulation, a suitable precursor is prepared by pre-spraying and can then be initially introduced in the fluidised-bed granulator for the actual co-spray-granulation, the main spraying:

1. Pre-spraying: 0.20 kg of mannitol and 0.25 kg of sorbitol are dissolved in 2.20 kg of demineralised water at 20-25° C. with stirring. 1.75 kg of calcium hydrogenphosphate dihydrate are subsequently suspended in the clear solution with stirring.

0.3 kg of mannitol powder is initially introduced in a fluidised-bed granulator as described, for example, in WO 00/76650 A1 or as marketed by Glatt (GPCG 5, Glatt, Germany) and fluidised. The spray suspension described is sprayed onto this fluidised bed.

In order to carry out this co-spray-granulation, the following settings are carried out in order to control the GPCG 5 fluidised-bed granulator:

feed-air flap: about 20% (about 225 m³/h),
exhaust-air flap: about 25%,
feed-air temperature: about 70° C.,
nozzle: as two-component nozzle 1.2 mm in top down, upper nozzle position, spray pressure 3.5 bar,
spray rate: increasing from 0.02 kg/minute to 0.12 kg/minute,
exhaust-air temperature setting: about 40° C.
When the spraying is complete, the resultant material is dried for about a further 10 to 20 minutes in the fluidised bed, with the temperature of the feed air being set so that the product temperature increases to 50° C.

2. Main spraying: 0.50 kg of mannitol and 0.25 kg of sorbitol are added to 2.50 kg of demineralised water with stirring. 1.75 kg of calcium hydrogenphosphate dihydrate are added to the clear solution obtained in this way. The suspension formed is stirred for about a further hour in order to destroy any agglomerates formed.

0.5 kg of the pre-spraying is initially introduced in the fluidised-bed granulator (GPCG 5), and the suspension is—as described above with reference to the preparation of the pre-spraying—sprayed on.

This first main spraying can be followed by a plurality of further sprayings, where in each case only a small part of the preceding spraying is initially introduced in the fluidised bed for each spraying, for example 0.5 kg as described above. In this way, the "non-co-sprayed" content in the product is continuously reduced.

The complete drying of the product is checked via the complexometric calcium determination (as in-process check). At the same time, this determination also allows any "overdrying" of the calcium hydrogenphosphate dihydrate, i.e. any loss of water of crystallisation, to be recognised.

Experimental Results

The results achieved by the various experiments are shown in Tables 1-5 below.

Table 1 shows the tested compositions with different proportions by weight of calcium hydrogenphosphate dihydrate, mannitol and sorbitol.

Table 2 contains the physical data determined for the tested compositions.

Table 4 shows the corresponding physical data for commercially available directly compressible calcium hydrogenphosphate hydrates and a tabletted mechanical mixture of DC calcium hydrogenphosphate dihydrate, mannitol and sorbitol.

Table 3 shows the tabletting data, pressing force, tablet hardness, friability, disintegration time, ejection force of the tested compositions. Table 5 shows the corresponding tabletting data for commercially available DC calcium hydrogenphosphate dihydrates compared with those of the particularly preferred co-spray-granulated combinations of calcium hydrogenphosphate dihydrate, mannitol and sorbitol of Examples E and D.

Figure 1:
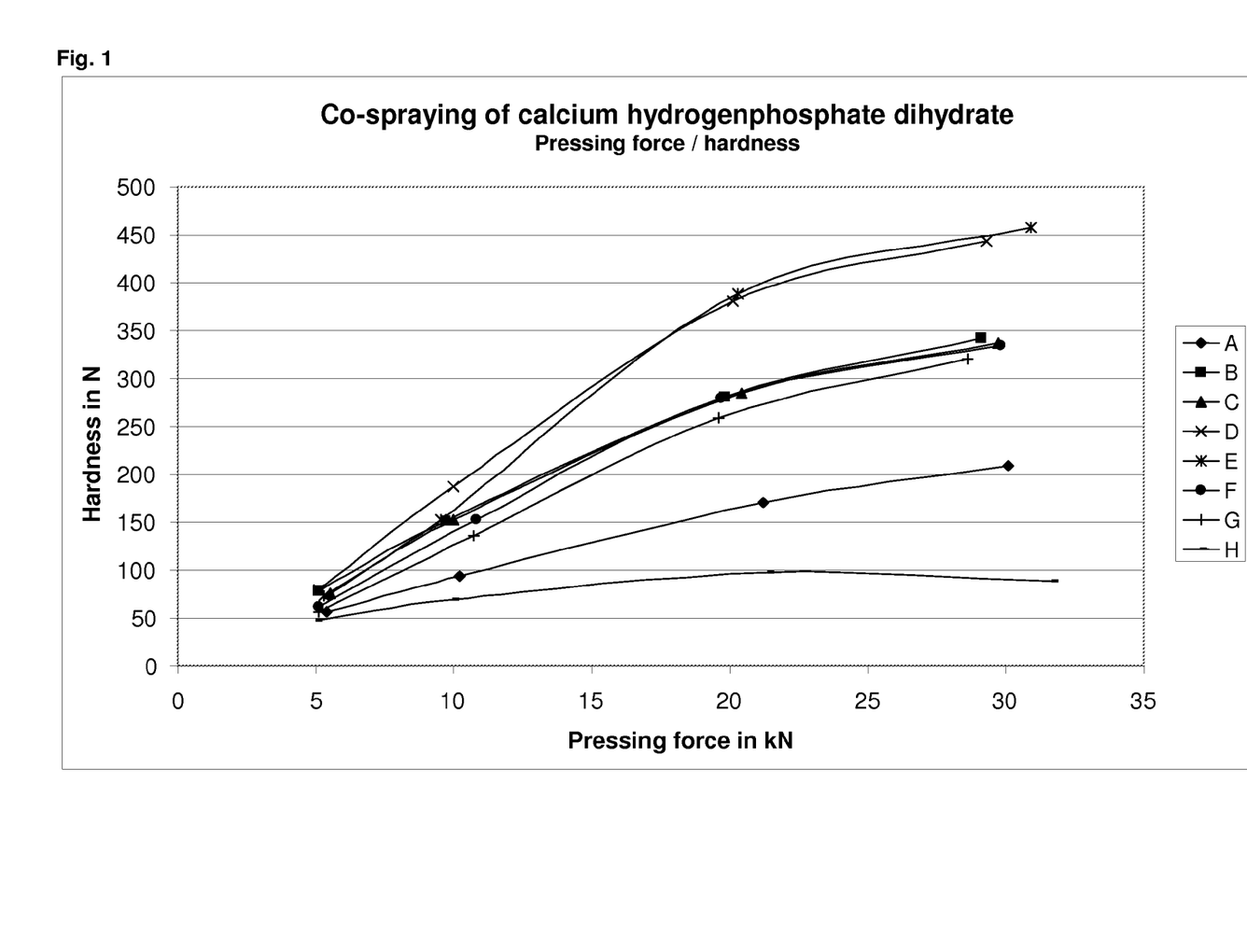
FIG. 1 illustrates the co-spraying of calcium hydrogenphosphate dehydrate; pressing force/hardness.

FIG. 1 shows a comparison of the pressing force/hardness profiles for the co-sprayed calcium hydrogenphosphate dihydrate compositions investigated. It can be seen from the profiles that on pressing of co-spray-granulated calcium hydrogenphosphate dihydrate with small amounts of added mannitol/sorbitol (Example H) to give tablets with increasing pressing pressure, the tablet hardnesses only vary between about 50 and 100 N. If, however, a co-sprayed composition comprising 70% by weight of calcium hydrogenphosphate dihydrate and 30% by weight of mannitol is tabletted with increasing pressing pressure under the same conditions, products having hardnesses of between about 50 and 220 N are obtained. For the other compositions investigated, tablets having even significantly higher hardnesses are obtained under the same conditions. Particularly high hardnesses are achieved, in particular, for compositions in which the calcium hydrogenphosphate dihydrate:mannitol:sorbitol weight ratio is 60:30:10 or 70:20:10.

Figure 3:
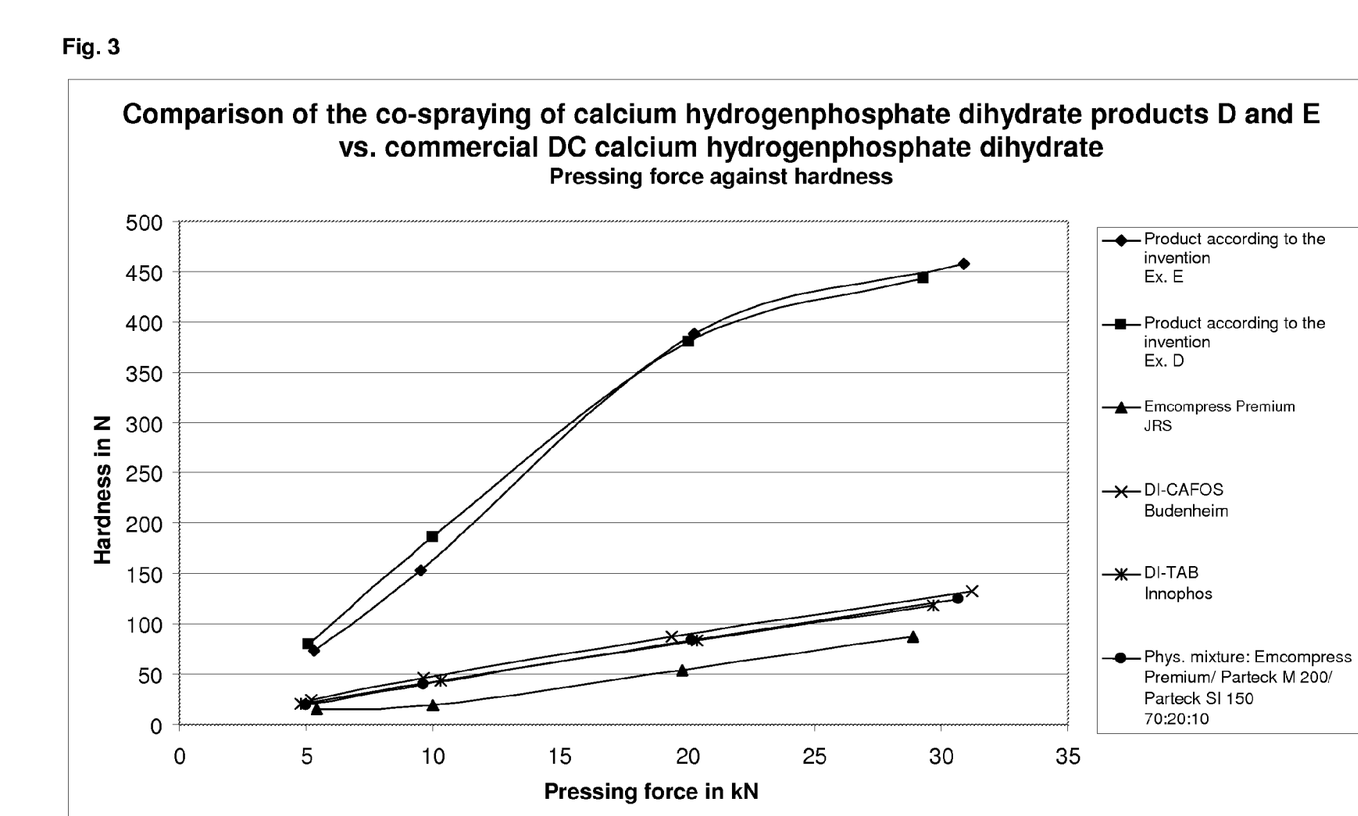
FIG. 3 illustrates the comparison of the co-spraying of calcium hydrogenphosphate dihydrate products D and E vs. commercial DC calcium hydrogenphosphate dehydrate; pressing force against hardness.

As shown in FIG. 3, a comparison of the compositions according to the invention with commercially available directly tablettable calcium hydrogenphosphate dihydrate grades shows that, in particular for compositions in which the calcium hydrogenphosphate dihydrate:mannitol:sorbitol weight ratio is 60:30:10 or 70:20:10, considerably higher tablet hardnesses are achieved at the same pressing forces. However, this also applies to compositions in which calcium hydrogenphosphate dihydrate has been co-sprayed with at least one of the polyols mannitol or sorbitol, as shown in the comparison between compositions A and B and the pure substances in FIGS. 1 and 3. This is particularly surprising compared with physical mixtures of DC calcium hydrogenphosphate dihydrate, DC mannitol and DC sorbitol. These exhibit only comparatively slightly increased tablet hardnesses compared with the tabletted pure substances at various pressing forces.

Figure 2:
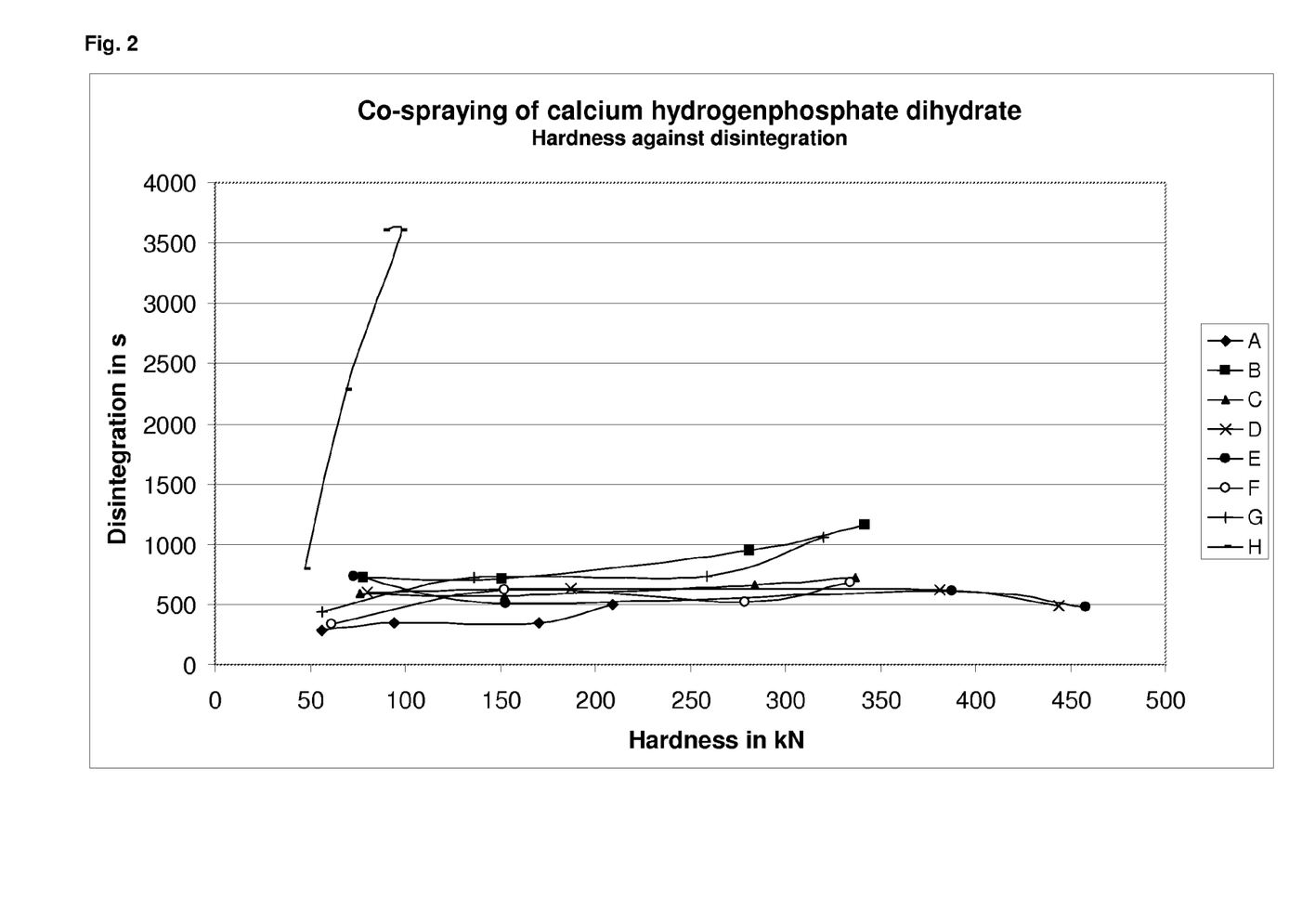
FIG. 2 illustrates the co-spraying of calcium hydrogenphosphate dehydrate; hardness against disintegration.
Figure 4:
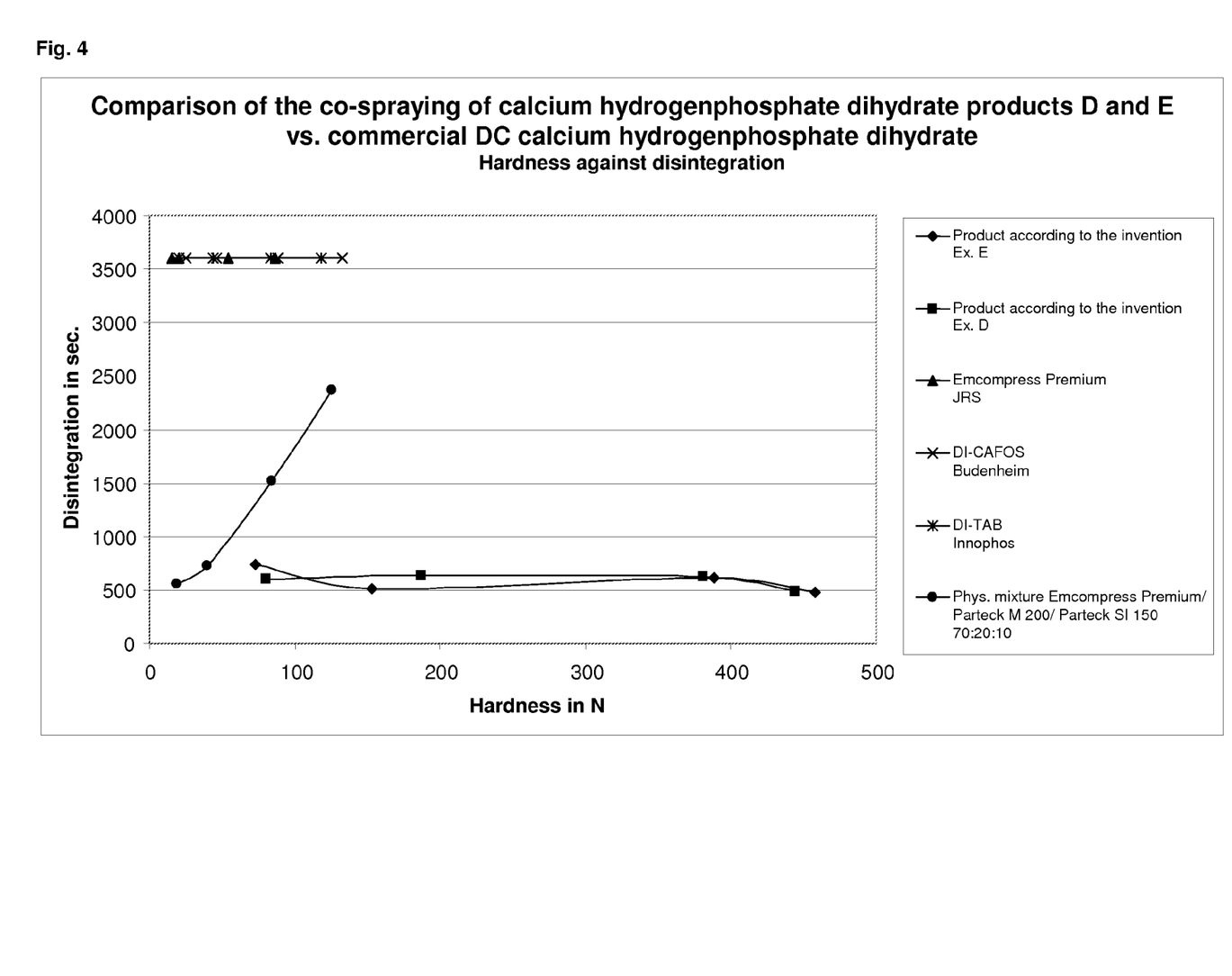
FIG. 4 illustrates the comparison of the co-spraying of calcium hydrogenphosphate dihydrate products D and E vs. commercial DC calcium hydrogenphosphate dehydrate; hardness against disintegration.

In spite of the increased tablet hardnesses, the corresponding tablets of the compositions according to the invention have very short disintegration times compared with the pure substance, as can be seen very well from the graphical representations in FIG. 2 and FIG. 4. Whereas a tabletted composition consisting of 90% by weight of calcium hydrogenphosphate dihydrate and 5% by weight of each of mannitol and sorbitol exhibits an enormously increased disintegration time of more than 3600 sec with increasing hardness of between 47 and 89 N, the compositions according to the invention only have disintegration times in the range from about 300 sec to 750 sec, in spite of increasing hardness, apart from disintegration times of 900 to 1160 sec for compositions consisting of 70% by weight of calcium hydrogenphosphate dihydrate and 30% by weight of sorbitol with a hardness of 342 N and for compositions consisting of 85% by weight of calcium hydrogenphosphate dihydrate and 10% by weight of mannitol and 5% by weight of sorbitol.

Whereas the disintegration times of the tablets made from physical mixtures of DC calcium hydrogenphosphate dihydrate, DC mannitol and DC sorbitol increase with increasing hardness, as shown by FIG. 4, the disintegration times of the compositions according to the invention change comparatively little with increasing hardnesses, or remain virtually constant in the case of particularly preferred compositions D and E. Although the disintegration times of the tablets made from commercially available calcium hydrogenphosphate dihydrate grades also remain approximately constant with increasing hardnesses, they are basically a multiple higher, i.e. whereas tablets produced from compositions according to the invention have disintegration times in the range from 300 to 1160 sec, tablets of commercially available calcium hydrogenphosphate dihydrate grades exhibit disintegration times of longer than 3600 sec.

Figure 5:
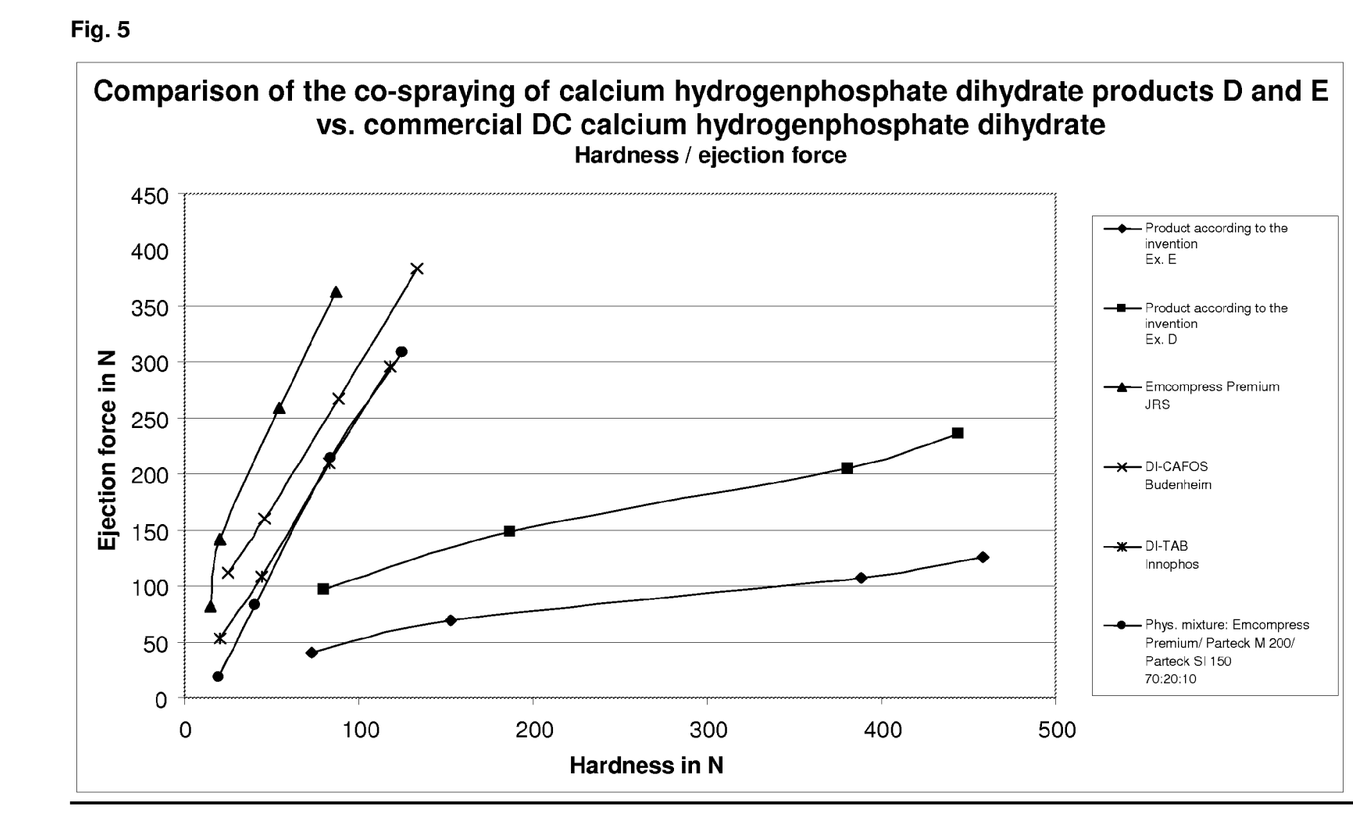
FIG. 5 illustrates the comparison of the co-spraying of calcium hydrogenphosphate dihydrate products D and E vs. commercial DC calcium hydrogenphosphate dehydrate; hardness/ejection force.

In FIG. 5, the hardnesses of the tablets produced are plotted against the ejection forces. By way of example here, the hardnesses of tablets produced from compositions of Examples D and E and the associated ejection forces are compared with those of corresponding commercially available products. This comparison shows quite vividly that tablets made from compositions according to the invention can be ejected from the tabletting moulds with ejection forces which increase relatively little, in spite of increasing hardness. The corresponding comparative data are also shown in Table 5. By contrast, the requisite ejection forces for the commercially available products compared increase very considerably, even with a fairly small increase in the tablet hardness. Accordingly, the stressing of the tabletting machines is significantly less on use of the directly compressible compositions according to the invention compared with the use of commercially available compositions.

TABLE 1

| Product | Calcium hydrogenphosphate dihydrate Art. No.: 1.2146 Merck KGaA, Germany [% by weight] | Mannitol Art. No.: 1.05980 Merck KGaA, Germany [% by weight] | Sorbitol (Parteck SI 400) Art. No.: 1.03140 Merck KGaA, Germany [% by weight] |
|---|---|---|---|
| A | 70 | 30 | |
| B | 70 | | 30 |
| C | 50 | 40 | 10 |
| D | 60 | 30 | 10 |
| E | 70 | 20 | 10 |
| F | 80 | 15 | 5 |
| G | 85 | 10 | 5 |
| H | 90 | 5 | 5 |

TABLE 2

| | A | B | C | D | E | F | G | H |
|---|---|---|---|---|---|---|---|---|
| Bulk density [g/ml] | 0.70 | 0.59 | 0.63 | 0.60 | 0.66 | 0.70 | 0.71 | 0.68 |
| Tapped density [g/ml] | 1.00 | 0.71 | 0.77 | 0.76 | 0.78 | 0.88 | 0.85 | 0.79 |
| Flow angle [°] | 41.3 | 31.8 | 32.6 | 29.1 | 29.6 | 34.7 | 33.1 | 34.7 |
| Hausner factor | 1.43 | 1.20 | 1.22 | 1.27 | 1.18 | 1.26 | 1.20 | 1.16 |
| Compressibility index [%] | 30.00 | 16.90 | 18.18 | 21.05 | 15.39 | 20.46 | 16.47 | 13.92 |
| Particle-size distribution [% by weight] | | | | | | | | |
| <32 μm | 33.63 | 0 | 0 | 0.07 | 0 | 0.09 | 0 | 0.02 |
| 32-50 μm | 38.11 | 0.07 | 1.92 | 1.98 | 2.62 | 6.78 | 2.02 | 0.51 |
| 50-100 μm | 19.54 | 0.41 | 8.36 | 17.82 | 16.96 | 46.06 | 36.56 | 7.63 |
| 100-200 μm | 5.92 | 2.85 | 30.76 | 67.36 | 34.00 | 39.47 | 48.75 | 9.81 |
| 200-315 μm | 1.15 | 30.05 | 43.35 | 11.61 | 35.31 | 3.26 | 6.17 | 12.00 |
| 315-500 μm | 0.62 | 39.14 | 11.92 | 0.64 | 8.90 | 1.86 | 4.45 | 32.07 |
| 500-710 μm | 0.35 | 27.30 | 2.75 | 0.31 | 2.21 | 0.84 | 1.74 | 22.32 |
| 710-1000 μm | 0.33 | 0.18 | 0.90 | 0.09 | 0 | 0.92 | 0.31 | 15.35 |
| >1000 μm | 0.35 | 0 | 0.04 | 0.12 | 0 | 0.72 | 0 | 0.29 |
| Calcium content [%] | | | | | | | | |
| theoretical | 16.3 | 16.3 | 11.7 | 14.0 | 16.3 | 18.6 | 19.8 | 21.0 |
| found | 16.7 | 16.8 | 12.0 | 14.0 | 16.5 | 18.7 | 20.0 | 20.8 |

TABLE 3

| Co-sprayed product | Pressing force [kN] nom. | Pressing force [kN] actual | Tablet hardness [N] | Friability [%] | Disintegration time [sec] | Ejection force [N] |
|---|---|---|---|---|---|---|
| A | 5 | 5.4 | 56 | 1.05 | 286 | 75 |
| | 10 | 10.2 | 94 | 0.335 | 341 | 140 |
| | 20 | 21.2 | 170 | 0.172 | 351 | 292 |
| | 30 | 30.1 | 209 | 0.145 | 497 | 393 |
| B | 5 | 5.1 | 78 | 0.059 | 725 | 76 |
| | 10 | 9.7 | 151 | 0.264 | 717 | 119 |
| | 20 | 19.8 | 281 | 0.103 | 948 | 179 |
| | 30 | 29.1 | 342 | 0.103 | 1158 | 200 |
| C | 5 | 5.5 | 76 | 0.106 | 589 | 74 |
| | 10 | 10.0 | 152 | 0.066 | 566 | 118 |
| | 20 | 20.4 | 284 | 0.084 | 662 | 175 |
| | 30 | 29.7 | 337 | 0.093 | 727 | 208 |
| D | 5 | 5.1 | 80 | 0.245 | 602 | 97 |
| | 10 | 10.0 | 187 | 0.132 | 631 | 148 |
| | 20 | 20.1 | 381 | 0.111 | 623 | 205 |
| | 30 | 29.3 | 444 | 0.129 | 490 | 236 |
| E | 5 | 5.3 | 73 | 0.019 | 732 | 40 |
| | 10 | 9.5 | 153 | 0.014 | 505 | 69 |
| | 20 | 20.3 | 388 | 0.059 | 613 | 107 |
| | 30 | 30.9 | 458 | 0.080 | 474 | 125 |
| F | 5 | 5.1 | 61 | 0.129 | 336 | 63 |
| | 10 | 10.8 | 152 | 0.103 | 621 | 108 |
| | 20 | 19.7 | 279 | 0.114 | 523 | 160 |
| | 30 | 29.8 | 334 | 0.118 | 687 | 201 |
| G | 5 | 5.1 | 56 | 0.133 | 434 | 49 |
| | 10 | 10.7 | 136 | 0.108 | 726 | 95 |
| | 20 | 19.6 | 259 | 0.100 | 734 | 155 |
| | 30 | 28.6 | 320 | 0.102 | 1059 | 199 |
| H | 5 | 5.0 | 47 | 0.173 | 794 | 51 |
| | 10 | 10.0 | 69 | 0.150 | 2278 | 87 |
| | 20 | 21.4 | 98 | 0.149 | >3600 | 156 |
| | 30 | 31.7 | 89 | 0.118 | >3600 | 165 |

TABLE 4

| | Emcompress Premium | DI-CAFOS | DI-TAB | Emcompress Premium/Parteck M 200/Parteck SI 150 70:20:10 mech. mixture |
|---|---|---|---|---|
| Bulk density [g/ml] | 0.72 | 0.84 | 0.82 | 0.70 |
| Tapped density [g/ml] | 0.90 | 1.02 | 1.03 | 0.86 |
| Flow angle [°] | 31.8 | 29.6 | 30.1 | 30.6 |
| Hausner factor | 1.25 | 1.21 | 1.26 | 1.23 |
| Compressibility index [%] | 20.00 | 17.65 | 20.39 | 18.61 |
| Particle-size distribution [% by weight] | | | | |
| <32 μm | 0.02 | 0.10 | 0.02 | 0 |
| 32-50 μm | 1.62 | 1.29 | 1.79 | 1.54 |
| 50-100 μm | 15.64 | 9.76 | 13.35 | 19.50 |
| 100-200 μm | 67.62 | 72.14 | 41.45 | 60.24 |

TABLE 4-continued

|  | Emcompress Premium | DI-CAFOS | DI-TAB | Emcompress Premium/Parteck M 200/Parteck SI 150 70:20:10 mech. mixture |
|---|---|---|---|---|
| 200-315 μm | 14.71 | 16.48 | 42.93 | 17.14 |
| 315-500 μm | 0.32 | 0.23 | 0.42 | 1.32 |
| 500-710 μm | 0.05 | 0 | 0.02 | 0.16 |
| 710-1000 μm | 0.02 | 0 | 0.02 | 0.05 |
| >1000 μm | 0 | 0 | 0 | 0.05 |

TABLE 5

| | Pressing force [kN] | | Tablet hardness [N] | Friability [%] | Disintegration time [sec.] | Ejection force [N] |
|---|---|---|---|---|---|---|
| Product | nom. | actual | | | | |
| Product according to the invention Ex. E | 5 | 5.3 | 73 | 0.019 | 732 | 40 |
| | 10 | 9.5 | 153 | 0.014 | 505 | 69 |
| | 20 | 20.3 | 388 | 0.059 | 613 | 107 |
| | 30 | 30.9 | 458 | 0.080 | 474 | 125 |
| Product according to the invention Ex. D | 5 | 5.1 | 80 | 0.245 | 602 | 97 |
| | 10 | 10 | 187 | 0.132 | 631 | 148 |
| | 20 | 20.1 | 381 | 0.111 | 623 | 205 |
| | 30 | 29.3 | 444 | 0.129 | 490 | 236 |
| Emcompress Premium JRS | 5 | 5.4 | 15 | 100 | >3600 | 82 |
| | 10 | 10.0 | 20 | 90.239 | >3600 | 141 |
| | 20 | 19.8 | 54 | 0.632 | >3600 | 259 |
| | 30 | 28.9 | 87 | 0.350 | >3600 | 362 |
| DI-CAFOS Budenheim | 5 | 5.2 | 25 | 31.07 | >3600 | 112 |
| | 10 | 9.6 | 46 | 0.507 | >3600 | 160 |
| | 20 | 19.4 | 88 | 0.293 | >3600 | 267 |
| | 30 | 31.2 | 133 | 0.188 | >3600 | 383 |
| DI-TAB Innophos | 5 | 4.8 | 20 | 100 | >3600 | 53 |
| | 10 | 10.3 | 44 | 0.612 | >3600 | 108 |
| | 20 | 20.4 | 83 | 0.279 | >3600 | 209 |
| | 30 | 29.7 | 118 | 0.192 | >3600 | 296 |
| Physical mixture of Emcompress Premium/ Parteck M 200/ Parteck SI 150, 70:20:10 | 5 | 5.0 | 19 | 4.282 | 555 | 18 |
| | 10 | 9.6 | 40 | 1.223 | 725 | 83 |
| | 20 | 20.2 | 84 | 0.474 | 1517 | 214 |
| | 30 | 30.7 | 125 | 0.174 | 2366 | 309 |

The invention claimed is:

1. A directly compressible tableting composition, comprising calcium hydrogenphosphate dihydrate:mannitol:sorbitol in a weight ratio in the range between 60:30:10 and 85:10:5 and a
    wherein said composition has a flow angle in the range from 29 to 42° and a bulk density in the range 0.55-0.75 g/ml with a tapped density in the range 0.73-0.90 g/ml.

2. The directly compressible tableting composition according to claim 1 for the production of tablets, further comprising xylitol or erythritol.

3. The directly compressible composition according to claim 1 for the production of tablets, wherein said calcium hydrogenphosphate dihydrate and mannitol and sorbitol are co-spray granulated.

4. The directly compressible tableting composition according to claim 1, comprising a flow angle in the range from 29 to 35°.

5. A composition according to claim 4, comprising a flow angle in the range from 29 to 30°.

6. The directly compressible tableting composition according to claim 1, comprising a particle-size distribution of 8 to 47% by weight in the range from 50 to 100 μm, 30 to 68% by weight in the range 100 to 200 μm, 6 to 44% by weight in the range from 200 to 315 μm and 0.6 to 12% by weight in the range 315-500 μm, where the proportion by weight of the particle-size fraction <50 μm is not more than 7% by weight and the proportion by weight of the particle-size fraction >500 μm is not more than 4% by weight.

7. The directly compressible composition according to claim 1, comprising a calcium content in the range from 11 to 20% by weight.

8. The directly compressible tableting composition according to claim 1, wherein after compression with a pressing force of 20 kN, tablets having hardnesses of >250 N, together with an ejection force of <210 N, a friability of <0.12%, a disintegration time of <735 seconds.

9. The directly compressible tableting composition according to claim 1, wherein after compression with a pressing force of 20 kN, pressed tablets having hardnesses of >300 N, together with an ejection force of <110 N, a friability of <0.06% and a disintegration time of <620 seconds.

10. The directly compressible composition according to claim 1, wherein after compression with a pressing force of 30 kN, pressed tablets having hardnesses of >430 N, together with an ejection force of <130 N, a friability of at most 0.08% and a disintegration time of <480 seconds.

11. A process for the preparation of directly compressible compositions for the production of tablets according to claim 1, wherein a solution or suspension comprising calcium hydrogenphosphate dihydrate, mannitol and sorbitol in a weight ratio to one another in the range from 60:30:10 and 85:10:5 in water, where 4 parts of solid are dissolved or suspended in 4 parts of water, is subjected to a co-spray-granulation process, either batchwise or continuously in a fluidised-bed granulator.

* * * * *